(12) United States Patent
Migliorini et al.

(10) Patent No.: US 8,900,880 B2
(45) Date of Patent: Dec. 2, 2014

(54) VIRAL CITRULLINATED PEPTIDES AND USES THEREOF

(75) Inventors: Paola Migliorini, Siena (IT); Federico Pratesi, Siena (IT)

(73) Assignee: Toscana Biomarkers S.R.L., Siena (IT)

(*) Notice: Subject to any disclaimer, the term of this patent is extended or adjusted under 35 U.S.C. 154(b) by 0 days.

(21) Appl. No.: 13/510,091

(22) PCT Filed: Nov. 22, 2010

(86) PCT No.: PCT/IB2010/055347
§ 371 (c)(1),
(2), (4) Date: May 16, 2012

(87) PCT Pub. No.: WO2011/061720
PCT Pub. Date: May 26, 2011

(65) Prior Publication Data
US 2013/0017560 A1    Jan. 17, 2013

(30) Foreign Application Priority Data

Nov. 23, 2009 (EP) .................................. 09176776

(51) Int. Cl.
| | | |
|---|---|---|
| G01N 33/564 | (2006.01) | |
| C07K 14/00 | (2006.01) | |
| C07K 14/05 | (2006.01) | |
| C07K 14/005 | (2006.01) | |
| A61K 38/00 | (2006.01) | |

(52) U.S. Cl.
CPC ..... *C07K 14/005* (2013.01); *C12N 2710/16222* (2013.01); *C12N 2710/16622* (2013.01); *A61K 38/00* (2013.01); *C07K 14/001* (2013.01)
USPC ........ 436/506; 424/186.1; 530/300; 530/326; 530/332

(58) Field of Classification Search
None
See application file for complete search history.

(56) References Cited

FOREIGN PATENT DOCUMENTS

| WO | 01/58481 A2 | 8/2001 |
|---|---|---|
| WO | 2004/087747 A2 | 10/2004 |
| WO | WO 2004087747 A2 * | 10/2004 |

OTHER PUBLICATIONS

Grazia Maria Luisa Rizzelli. Thesis, published 2006/2007 in Italian, machine translated. [Retrieved from the internet on May 13, 2013] <http://etd.adm.unipi.it/theses/available/etd-10022007-195210/unrestricted/TesiRizzelli.pdf>.*
F. Pratesi et al. Antibodies to a new viral citrullinated peptide, VCP2: fine specificity and correlation with anti-cyclic citrullinated peptide (CCP) and anti-VCP1 antibodies. 2011. Clinical and Experimental Immunology, 164: 337-345.*
Pratesi F et al. Deiminated Epstein-Barr virus nuclear antigen 1 is a target of anti-citrullinated protein antibodies in rheumatoid arthritis. Arthritis Rheum. Mar. 2006;54(3):733-41.*
GenBank: ABB89251.1, EBNA-1 [Human herpesvirus 4], Oct. 15, 2009, p. 1-2.*
GenBank: CAD53395.1, EBNA-2 nuclear protein [Human herpesvirus 4], May 15, 2008, p. 1-2.*
J P Tam. Synthetic peptide vaccine design: synthesis and properties of a high-density multiple antigenic peptide system. Proc Natl Acad Sci U S A. Aug. 1988; 85(15): 5409-5413.*
Incaprera, M., et al: "Potential role of the Epstein-Barr virus in systemic lupus erythematosus autoimmunity.", Clinical and Experimental Rheumatology, May-Jun. 1998, vol. 16, No. 3, May 1998, pp. 289-294.
Hazelton, R. A., et al: "The prevalence of antibodies to an epstein-barr virus-induced polypeptide EBNA-2 in the sera of rheumatoid arthritic families.", British Journal of Rheumatology, vol. 26, No. 3, 1987, pp. 193-196.
Yamazaki, M., et al: "Elevated immunoglobulin G antibodies to the proline-rich amino-terminal region of Epstein-Barr virus nuclear antigen-2 in sera from patients with systemic connective tissue diseases and from a subgroup of Sjogren's syndrome patients with pulmonary involvements.", Clinical and Experimental Immunology Mar. 2005, vol. 139, No. 3, Mar. 2005, pp. 558-568.
Gross, H., et al: "Asymmetric Arginine dimethylation of Epstein-Barr virus nuclear antigen 2 promotes DNA targeting", Virology, Academic Press,Orlando, US, vol. 397, No. 2, Feb. 20, 2010, pp. 299-310.

* cited by examiner

Primary Examiner — Mary E Mosher
Assistant Examiner — Nick Zou
(74) Attorney, Agent, or Firm — Lucas & Mercanti, LLP

(57) ABSTRACT

The present invention relates to an antigenically effective peptide comprising, from the amino to the carboxylic terminal, the amino acid sequence: G P P W W P P I C D P P Q P S K T Q G Q S $X_1$ G Q S $X_2$ G $X_3$ G $X_4$ G $X_5$ G $X_6$ G $X_7$ G K G K S $X_8$ D K Q $X_9$ K P G G P W $X_{10}$ P E P (SEQ ID No. 1), wherein the amino acids $X_1$-$X_{10}$ are selected independently from an arginine residue or a citrulline residue and at least one of $X_1$-$X_{10}$ is a citrulline residue, or a functional fragment thereof and uses thereof.

12 Claims, 4 Drawing Sheets

VIRAL CITRULLINATED PEPTIDES AND USES THEREOF

CROSS-REFERENCE TO RELATED APPLICATIONS

This application is a 371 of PCT/IB2010/055347, filed Nov. 22, 2010, which claims the benefit of European Patent Application No. 09176776.4, filed Nov. 23, 2009, the contents of each of which are incorporated herein by reference.

FIELD OF INVENTION

The present invention refers to novel citrullinated synthetic peptides derived from Epstein Barr virus and their use in the diagnosis and treatment of autoimmune diseases, particularly Rheumatoid Arthritis (RA).

STATE OF THE ART

In the broad spectrum of inflammatory joint diseases, rheumatoid arthritis (RA) has a prominent position. By causing symmetrical and destructive inflammation in the small and large joints, RA leads to pain and joint failure, eventually resulting in disfiguration and disability.

The occurrence of various autoantibodies is a hallmark of RA. The best known is rheumatoid factor (RF), a class of IgG or IgM antibodies directed against the Fc-region of the IgG isotype of immunoglobulins. About 70-80% of RA-patients are sero-positive for RF, but RFs are also found in chronic infections, lymphoproliferative diseases, other rheumatic diseases, and in nearly 20% of elderly healthy individuals. Thus, given the limited specificity of RF for RA, other more specific antibodies have been sought. APF (anti-perinuclear factor) antibodies and AKAs (anti-keratin antibodies) were clearly demonstrated to be highly disease specific.

The antigens recognized by APF antibodies and AKAs were later found to be citrulline-containing proteins post-translationally generated by modifying arginines into citrulline residues. An ELISA using synthetic citrullinated peptides (CPs) derived from filaggrin was developed [G. A. Schellekens et al. J. Clin. Invest. 1998, 101, 273]. To increase the sensitivity of the test, the CPs were modified to a structure, the cyclic citrullinated peptide (CCP), in which the citrulline moiety is optimally exposed for antibody binding [International application WO1998022503]. In a so-called CCP1 test [G. A. Schellekens et al. Arthritis Rheum. 2000, 43, 155], antibodies could be detected in 68% of sera from RA patients with a specificity of 98% with a single CCP. Recent studies indicate that the second generation of CCP test, CCP2 [J. Avouac et al. Ann. Rheum. Dis. 2006, 65, 845], is very sensitive and specific, showing a sensitivity of 68% (range 39-94%) with a specificity of 95% (range 81-100%). Recently, a third-generation assay was developed by INOVA [L. Lutteri et al. Clin. Chim. Acta 2007, 386, 76] and claimed to be a new more sensitive anti-CCP ELISA which maintains a specificity of 98%. These ELISA tests are all commercially available (Euro-Diagnostica, Arnhem, The Netherlands; Axis-Shield, Dundee, Scotland; INOVA, San Diego, USA).

In addition, a number of patent applications, referring to citrullinated proteins/peptides-based methods to detect antibodies in RA patients have been filed [US20020143143, US20070087380, EP1946109, US20070148704, WO2009007846, WO2009000077, WO2007017556, EP1456662, WO1999028344, WO2008132264].

Various citrullinated proteins have been described in the RA synovium, e.g., extravascular citrullinated fibrin [C. Masson-Bessière et al. J. Immunol. 2001, 166, 4177], collagen II [H. Burkhardt et al. Eur. J. Immunol. 2005, 35, 1643] and vimentin in macrophages [E. R. Vossenaar et al. Arthritis Rheum. 2004, 50, 3485]. Although filaggrin is not expressed in the synovium, its citrullinated derivatives have been used for the detection of anti-CP antibodies [US20090028885, U.S. Pat. No. 7,445,903, U.S. Pat. No. 6,890,720].

RA involves both genetic and environmental influences and viruses have long been suspected to promote the development of RA. To be likely candidates for a causal role in RA, viruses must be ubiquitous, persist within the body, show direct or indirect tropism for the joints, and be capable of altering host immune responses. The Epstein Barr virus (EBV) exhibits these characteristics. As a result, potential links between EBV and RA have been a focus of research for the last three decades [K. H. Costenbader et al. Arthritis Res. Ther. 2006, 8, 204]. It is known that patients with RA possess elevated levels of antibodies to latent and replicative EBV proteins and in particular to EBNA-1 (Epstein-Barr nuclear antigen 1). Moreover, the peripheral blood EBV load in RA patients is higher than in controls. A number of studies shed light on the possible etiological role of EBV in RA synovitis [S. Sawada et al. Autoimmun. Rev. 2005, 4, 106]. These studies led to the idea of exploring the immune response in RA patients using CP of viral origin. Antibodies specific for a peptide corresponding to the EBNA-1(35-58) sequence (viral citrullinated peptide 1, VCP1), containing citrulline in place of arginine, were detected in 50% of RA sera and in less than 5% of normal and disease control sera [F. Pratesi et al. Arthritis Rheum. 2006, 54, 733]. In addition, affinity purified anti-VCP1 antibodies from RA sera reacted with filaggrin-derived CP, deiminated fibrinogen and deiminated recombinant EBNA-1. The frequency of anti-VCP1 antibodies was determined in 627 serum samples, 300 from patients with RA and 327 from controls, including connective tissue diseases, chronic arthritides, and healthy donors. Anti-VCP1 antibodies were found in 45% of RA sera versus less than 5% of controls [C. Anzilotti et al. J. Rheumatol. 2006, 33, 647].

Incaprera et al. [Clin. and Exp. Rheum. 1998, 16(3), 289-294] discloses the potential role of EBV in systemic lupus erythematosus autoimmunity. In particular this document indicates that EBNA-2(354-373) recognizes anti-SmD1 IgG antibodies.

Citrullinated peptides based on the deiminated EBNA-1 (35-58) are the object of the international application WO2004087747 in which their use to detect antibodies in RA sera is described. This application also discloses that the use of multiple antigen peptide [MAP; J. P. Tam PNAS U.S.A. 1988, 85, 5409], containing at least 4 copies of the deiminated EBNA-1(35-58) as coating antigen in immunological assay for the detection of antibodies, allows to detect antibodies in 45% of RA sera with a specificity of 95%.

SUMMARY OF THE INVENTION

The present invention relates to novel citrullinated synthetic peptides derived from EBV and their use in diagnosis and treatment of autoimmune diseases, specifically RA. In particular, these sequences are derived from EBV proteins (e.g. EBNA-1, EBNA-2). The citrullinated peptides according to the invention have an amino acid sequence comprised into the sequence of the 320-375 a.a region of the EBNA-2 protein of the EBV (Swiss-Prot P12978). Surprisingly, the peptides as described in the invention and possessing a number of citrulline residues greater than one were demonstrated to be very suitable for the specific diagnosis of RA.

In order to increase the sensitivity, keeping intact the specificity of the assay, the authors of the present invention searched for other deiminated sequences of viral origin for the set up of RA diagnostic assays. To this end, peptide sequences derived from EBV proteins have been synthesised with different degrees of arginine/citrulline substitutions and tested for reactivity in RA patients sera (Table 1). Among these, some sequences allowed the discrimination of RA sera from normal controls. The best results were obtained with citrullinated peptides derived from the deiminated peptide EBNA-2(338-358) (G Q S R G Q S R G R G R G R G R G K G). These sequences and their use in diagnosis and treatment of autoimmune disorders are the object of the present invention. In particular, the present invention shows that non citrullinated EBNA-2(338-358) does not react with RA sera. By contrast, the citrullinated peptides of the invention display an increased reactivity towards RA sera. It also demonstrates that the IgG population identified by the peptides of the invention is characterised as being RA-specific anti-CP IgGs and not SLE-specific anti-SmD1 IgGs. The present invention also identified two epitopes represented by the Gly-Cit repeats and the other in the Gly-Gln-Ser-Cit repeats, with the positions Cit-341, Cit-345 and Cit-349 being the most reactive.

The peptides of the invention derive from EBNA-2(320-375) region.

It is therefore an object of the present invention an antigenically effective peptide comprising, from the amino to the carboxylic terminus, the amino acid sequence: G P P W W P P I C D P P Q P S K T Q G Q S $X_1$ G Q S $X_2$ G $X_3$ G $X_4$ G $X_5$ G $X_6$ G $X_7$ G K G K S $X_8$ D K Q $X_9$ K P G G P W $X_{10}$ P E P (Formula I, SEQ ID No. 1), wherein the amino acids $X_1$-$X_{10}$ are selected independently from an arginine residue or a citrulline residue and at least one of $X_1$-$X_{10}$ is a citrulline residue, or a functional fragment thereof.

Preferably, the peptide comprises the amino acid sequence G Q S $X_1$ G Q S $X_2$ G $X_3$ G $X_4$ G $X_5$ G $X_6$ G K G (Formula II, a.a. 19 to a.a. 39 of SEQ ID No. 1) wherein the amino acids $X_1$-$X_7$ are selected independently from an arginine residue or a citrulline residue, and at least one of $X_1$-$X_7$ is a citrulline residue, or a functional fragment thereof.

Still preferably, the peptide comprises the amino acid sequence G Q S Cit G Q S Cit G $X_3$ G Cit G $X_5$ G $X_6$ G $X_7$ G K G (SEQ ID No. 27) wherein the amino acids $X_3$-$X_7$ are selected independently from an arginine residue or a citrulline residue. Still preferably, the peptide comprises the amino acid sequence selected from the group of:

GQSRGQSCitGRGRGRGRGRGKG (SEQ ID No. 4), GQSRGQSRGRGCitGRGRGRGKG (SEQ ID No. 6), GQS-RGQSCitGRGCitGRGRGRGKG (SEQ ID No. 12), GQSCitGQSCitGRGCitGRGRGRGKG (SEQ ID No. 22) or G Q S Cit G Q S Cit G Cit G Cit G Cit G Cit G Cit G K G (SEQ ID No. 2) wherein Cit is a citrulline residue, a functional fragment thereof.

In a preferred embodiment the peptide is of linear form. Still preferably the peptide is in the form of multimeric branched peptide or of other conjugated complex.

The multimeric branched peptide consists of:
a MAP nucleus structure;
a linear peptide having an amino acid sequence of formula I, II and/or IV, bonded through a carbamido link to each of amino terminal residues of the MAP nucleus structure, wherein the linear peptides are equal or different each others.

According to the invention a MAP nucleus structure is:

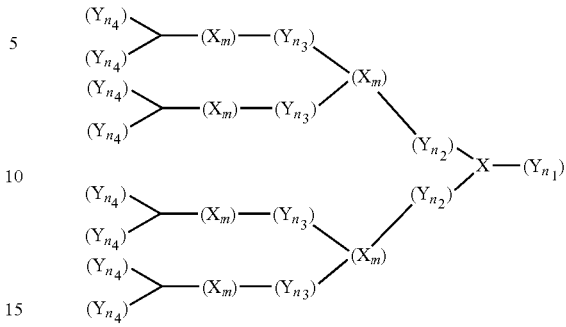

wherein X is an amino acid having at least two amino functional residues, Y is an amino acid selected from the group of alanine and/or glycine and/or lysine and/or a molecule used as spacer, m is 0 or 1, $n_1$ $n_2$ $n_3$ $n_4$ are integer numbers comprised between 0 and 10, and wherein bond are carbamido bonds.

A MAP or conjugate comprising a plurality of copies of a citrullinated linear synthetic peptide or of an antigenically effective fragment derived therefrom as described above, bound to an immunologically inert amino-acid core, therefore also falls within the scope of the present invention.

Preferably, the multimeric branched peptide comprises four identical copies of the peptide of the invention.

Still preferably the multimeric branched peptide is (G Q S Cit G Q S Cit G Cit G Cit G Cit G Cit G Cit G K G)$_4$ K$_2$ K beta-Alanine:

wherein Cit is a citrulline residue.

The peptides as above disclosed in free form or bound to appropriate resins, can be used for the treatment of patients affected by autoimmune disease such as RA as, thanks to their high specificity in the antibody recognition, they can be used to selectively remove antibody and also as immunomodulator of the disease.

Therefore, it is a further object of the invention the peptide as defined above for medical use. Preferably for use as anti-autoimmune disease agent.

The peptides as described in the invention are reactive with specific antibodies present in sera of autoimmune patients, in particular RA patients. An antibody present in the biological fluids of autoimmune patients will bind to the peptides of the invention. As indicated above, the citrullinated peptides of the invention, both in linear form and in MAP form, are particularly suitable to be used as antigens in an assay to detect the presence and/or to measure the levels of autoimmune disease-specific antibodies, such as anti-CP antibodies, in a sample of a biological fluid.

In order to perform the assay, the peptides can be adsorbed or covalently linked or modified with a carrier to bind it to a solid support (e.g. chips, microspheres, gold, polystyrene, reactor vessels or wells, micro-titre plate). In a first step of the method, the sample of biological fluid to be analyzed is placed in contact and incubated with the peptide of the invention that may be linked to the solid support. Any autoimmune disease-specific antibody, such as anti-CP antibodies, that are possibly present in the sample are thus specifically bound to the peptide of the invention, producing an antigen/antibody complex. The anti-CP antibodies to be detected in the immunoassay are IgG, IgA, or IgM immunoglobulins. The evaluation of the presence and the quantity of the antigen/antibody complex can be performed with a spectroscopic, a piezoelectric, or an electrochemical biosensor.

The above described method may be an ELISA immunological assay in which an indicator antibody, like an anti-human immunoglobulin, is conjugated to an enzyme and is added to measure the antibody titer by a spectroscopic transducer.

Thus, it is a further object of the invention a method for the diagnostic of an autoimmune disease in a subject comprising the step of detecting antibodies specific for the autoimmune disease in a biological sample by reacting under proper conditions said biological sample with at least one peptide as described above to produce a complex;

detecting the complex.

Higher sensitivity and specificity of the method is obtained when the peptides are used in the form of MAPs or of other conjugated complex. In particular in the form of tetravalent MAPs.

Thus, preferably the biological sample is reacted with at least one peptide of the invention and a peptide comprising the sequence (G G D N H G Cit G Cit G Cit G Cit G G G Cit P GAP G)$_4$ K$_2$ K beta-Alanine:

```
G G D N H G Cit G Cit G Cit G Cit G Cit G G G Cit P G A P G
                                                              \
                                                               K
                                                              /   \
G G D N H G Cit G Cit G Cit G Cit G Cit G G G Cit P G A P G        \
                                                                    K-betaA
                                                                   /
G G D N H G Cit G Cit G Cit G Cit G Cit G G G Cit P G A P G        /
                                                              \   /
                                                               K
                                                              /
G G D N H G Cit G Cit G Cit G Cit G Cit G G G Cit P G A P G
``` wherein: Cit=citrulline, or a functional fragment thereof.

It was found that a method based on the combined use of a MAP of citrullinated peptides of formula (I) and of MAP of deiminated EBNA-1(35-58) of sequence G G D N H G Cit G Cit G Cit G Cit G Cit G G G Cit P G A P G (formula III, SEQ ID No. 3) give the highest sensitivity and specificity test for detecting specific RA antibodies.

Thus preferably, the biological sample is reacted with the peptide comprising the sequence (G Q S Cit G Q S Cit G Cit G Cit G Cit G Cit G Cit G K G)$_4$ K$_2$ K beta-Alanine (Formula V, also named VCP-2):

```
G Q S Cit G Q S Cit G Cit G Cit G Cit G Cit G Cit G K G
                                                         \
                                                          K
                                                         /   \
G Q S Cit G Q S Cit G Cit G Cit G Cit G Cit G Cit G K G       \
                                                               K-betaA
                                                              /
G Q S Cit G Q S Cit G Cit G Cit G Cit G Cit G Cit G K G       /
                                                         \   /
                                                          K
                                                         /
G Q S Cit G Q S Cit G Cit G Cit G Cit G Cit G Cit G K G
``` wherein Cit=citrulline, or a functional fragment thereof and the peptide comprising the sequence (G G D N H G Cit G Cit G Cit G Cit G Cit G G G Cit P G A P G)$_4$ K$_2$ K beta-Alanine (Formula VI, also named VCP-1):

```
G G D N H G Cit G Cit G Cit G Cit G Cit G G G Cit P G A P G
                                                              \
                                                               K
                                                              /   \
G G D N H G Cit G Cit G Cit G Cit G Cit G G G Cit P G A P G        \
                                                                    K-betaA
                                                                   /
G G D N H G Cit G Cit G Cit G Cit G Cit G G G Cit P G A P G        /
                                                              \   /
                                                               K
                                                              /
G G D N H G Cit G Cit G Cit G Cit G Cit G G G Cit P G A P G
``` wherein: Cit=citrulline or a functional fragment thereof.

In a preferred embodiment the method is an immunological assay.

It is a further object of the invention a kit for the diagnostic of an autoimmune disease comprising at least one peptide of the invention, or a functional fragment thereof.

Preferably, the kit further comprises the peptide comprising the sequence (G G D N H G Cit G Cit G Cit G Cit G Cit G G G Cit P G A P G)$_4$ K$_2$ K beta-Alanine (Formula VI, also named VCP-1):

wherein: Cit=citrulline, or a functional fragment thereof.

In particular the kit allows the detection of anti-CP antibodies in biological fluids. The diagnostic kit comprises a combination of citrullinated peptides as defined above or of a functional fragment thereof, and at least one further reagent. Preferably, the further reagent is an anti-human immunoglobulin conjugated to an enzyme capable of reacting with a chromogenic substrate.

In the present invention, a preferred autoimmune disease is rheumatoid arthritis.

It is another object of the invention a pharmaceutical composition comprising a pharmaceutically acceptable and effective quantity of the peptide of the invention, or a functional fragment thereof.

In the present invention antigenically effective means that the peptide, or a functional fragment thereof is able to specifically bind autoimmune disease-specific antibodies and/or autoimmune disease-specific T cells.

BRIEF DESCRIPTION OF THE DRAWINGS

The invention will be now illustrated by means of illustrative, non limiting examples referring to the following figure.

DETAILED DESCRIPTION OF THE INVENTION

Example 1

Peptide Synthesis

Figure 1:
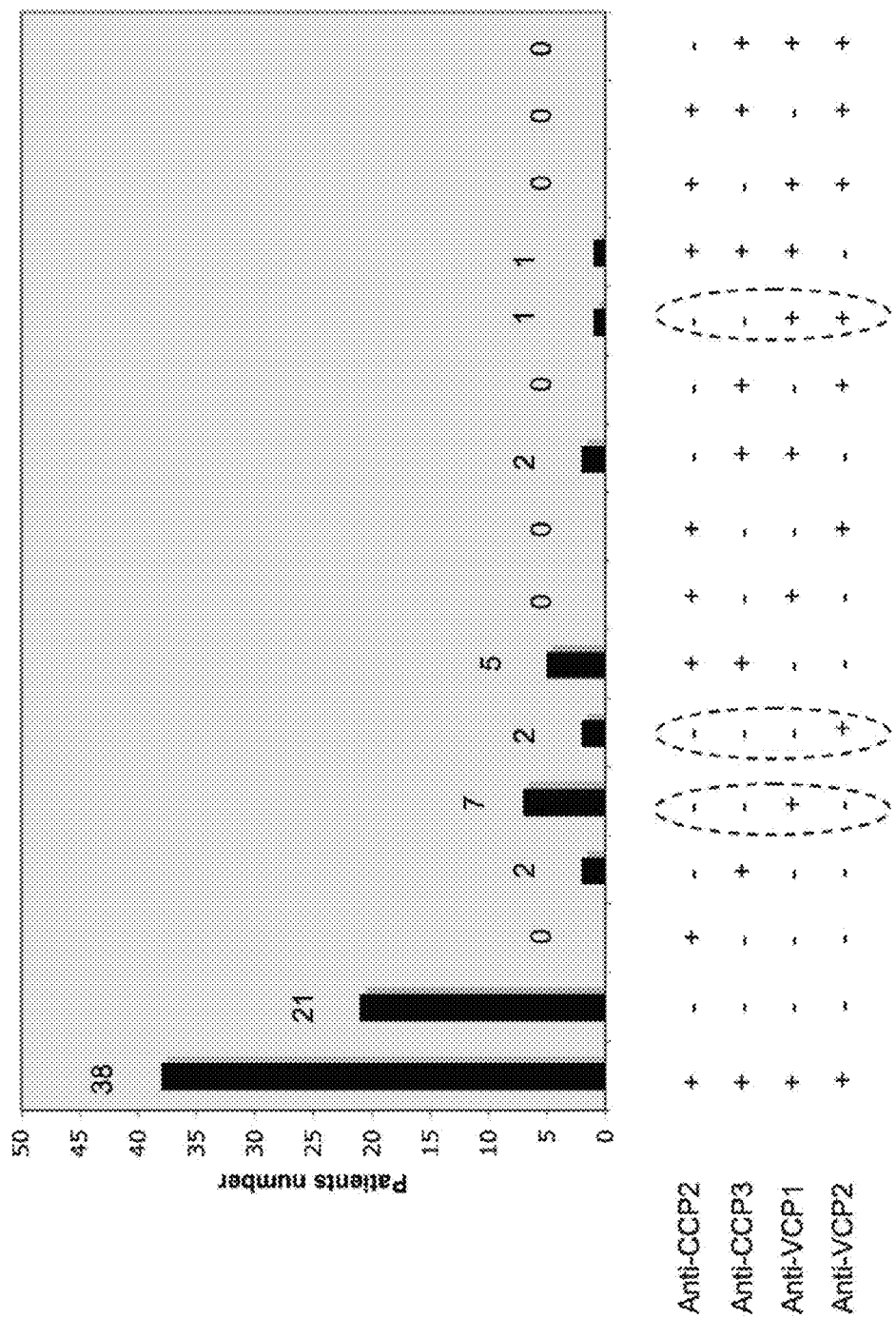
FIG. 1. 79 RA sera were tested by ELISA to evaluate the presence of different populations of autoantibodies comparing the reactivity towards the following antigens: CCP2, CCP3, VCP1 [peptide of formula (VI)], and VCP2 [peptide of formula (V)]. The presence of different populations of autoantibodies is depicted in the block diagram. Number of RA sera positive (+) or negative (−) to anti-CCP2, anti-CCP3, anti-VCP1 [peptide of formula (VI)], and anti-VCP2 [peptide of formula (V)] are shown above the diagram. The populations of antibodies positive to VCP1 [peptide of formula (VI)] and/or VCP2 [peptide of formula (V)], but not to CCP2 and CCP3, are highlighted.

Peptides were synthetized using a Wang resin preloaded with the C-terminal amino acid of the sequence or with the MAP core and following the Fmoc/tBu solid-phase peptide strategy. Fmoc deprotections were carried out in 20 min with 20% piperidine in DMF. Coupling reactions were performed by treating the resin for 45 min with a 0.5 M solution of the Fmoc-protected amino acids and HOBt in DMF (2.5 equiv), a 0.5 M solution of TBTU in DMF (2.5 equiv), and 4 M NMM in DMF (5 equiv). Peptide cleavage from the resin and deprotection of the amino acid side chains were carried out in 3 h with TFA/thioanisole/ethanedithiol/phenol/H$_2$O (82.5:5:2.5:5:5). The crude products were precipitated with cold Et$_2$O, centrifuged, and lyophilized. The pure peptides were obtained by HPLC in a purity >95% and characterized by mass spectrometry (ESI-Orbitrap and/or MALDI-TOF).

Example 2

ELISA for the Determination of Anti-CP Antibodies

The MAP of the citrullinated peptide antigens according to the invention was diluted to a concentration of 20 µg/ml in phosphate buffered saline (PBS) and loaded into the wells of a polystyrene micro-titration plate (50 µl/well). The plate was left overnight at +4° C. to permit interaction between peptide and plastics (however, it may be incubated at 37° C. for 1-2 hours with the same result). Upon completion of the coating period, the wells containing the antigen, plus an equal number of wells which were used as controls, were treated for 1 hour at room temperature (RT) with 3% bovine serum albumin (BSA) in PBS. The patients' serum samples (diluted 1:200 in a buffer constituted by 1% BSA, 0.05% Tween X-100 in PBS) were then loaded onto the plate (50 µl/well) and left to incubate for 3 hours at RT. After the incubation period, one washing was performed with 1% PBS Tween X-100 and two washings were performed with PBS (150 µl/well). An anti human-IgG, IgM or IgA antibody conjugated to the enzyme alkaline phosphatase (respectively diluted 1:3000, 1:1000 and 1:3000) in 1% PBS BSA, 0.05% Tween X-100, was used to show that the antigen/antibody reaction had taken place. The antibody (50 µl/well) was then incubated for 3 hours at RT with agitation. Upon completion of the incubation, after three washings as described above, the alkaline phosphatase substrate (p-nitrophenyl phosphate) was added to the wells and, in the presence of the enzyme, it produced a yellow product measurable by spectrophotometric techniques at a wavelength of 405 nm; its quantity was proportional to the titre of antibodies bound. The results of the test were expressed as the percentage of positivity, calculated by dividing the absorbance of each serum sample by the absorbance of a positive serum sample the value of which was set arbitrarily at 100.

Serum samples of 104 patients suffering from RA, 97 normal healthy subjects (NHS), and 194 disease controls (systemic lupus erythematosus, systemic scleroderma, Sjogren syndrome, mixed cryoglobulinemia, psoriasic arthritis, ankylosing spondilytis, rheumatic polymialgia and infectious mononucleosis) were tested by this method using the peptide of formula (V).

By considering each result that was greater than the 97.5th percentile of the normal control group to be positive, peptide of formula (V) anti-CP IgG antibodies were found in 67/104 (64%), IgM in 48/104 (46%) and IgA in 41/104 (40%) of the serum samples of patients with RA, and in less than 5% of normal healthy subjects and disease controls.

Example 3

Specificity of the Peptides in Respect to Other Autoimmune Diseases

Figure 2:
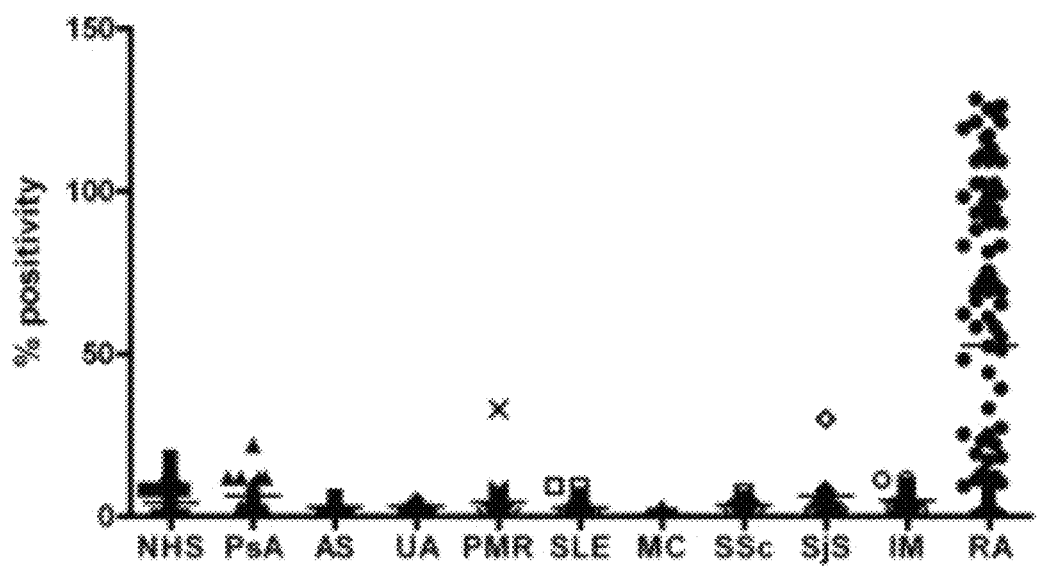
FIG. 2. Distribution of anti-citrullinated peptides/proteins antibodies (ACPA—anti-CP antibodies) detected with VCP2 in 100 RA, 100 normal healthy subjects (NHS) and 206 disease controls (ankylosing spondylitis, AS; infectious mononucleosis, IM; mixed cryoglobulinemia, MC; polymialgia rheumatica, PMR; psoriasic arthritis, PsA; Sjogren syndrome, SjS; systemic lupus erythematosus, SLE; systemic sclerosis, Ssc; undifferentiated arthritis, UA). Serum samples were tested by ELISA using the method described in example 2. Results demonstrate the high specificity of VCP2 in detecting ACPA in RA patients. Moreover, no antibodies were detected in disease controls and in particular in IM and SLE, in contrast with results described in Incaprera et al. [Clin Exp Rheumatol 1998, 16, 289], who reported the detection of IgGs with the non deiminated sequence EBNA2(354-373) in IM and SLE sera.

FIG. 2 shows the distribution of ACPA detected with VCP2 in 100 RA, 100 NHS and 206 disease controls (ankylosing spondylitis, AS; infectious mononucleosis, IM; mixed cryoglobulinemia, MC; polymialgia rheumatica, PMR; psoriasic arthritis, PsA; Sjogren syndrome, SjS; systemic lupus erythematosus, SLE; systemic sclerosis, Ssc; undifferentiated arthritis, UA). Serum samples were tested by ELISA using the method described in example 2. Results demonstrate the high specificity of VCP2 in detecting ACPA in RA patients. Moreover, no antibodies were detected in disease controls and in particular in IM and SLE, in contrast with results described in Incaprera et al. [Clin Exp Rheumatol 1998, 16, 289], who reported the detection of IgGs with the non deiminated sequence EBNA2(354-373) in IM and SLE sera.

Figure 3:
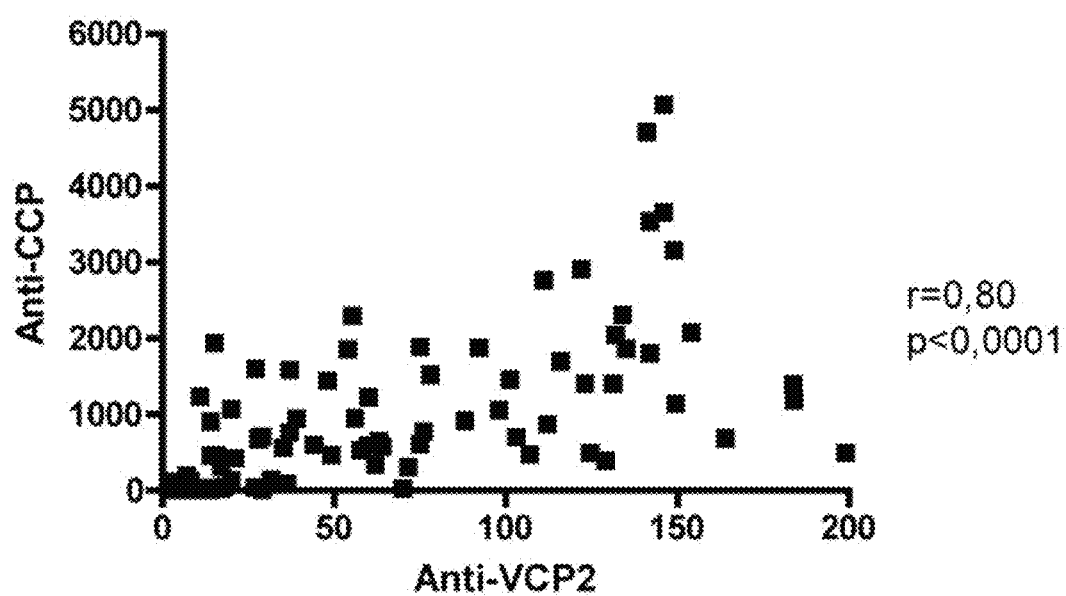
FIG. 3. Correlation between anti-CCP and anti-VCP2 antibodies. 100 RA sera were analyzed with CCP2 test and with VCP2 using the method described in example 2. Results show the significant correlation (p<0.0001) between the two populations of antibodies demonstrating that anti-VCP2 antibodies are ACPA and are thus specific for RA and not for other autoimmune diseases.

In addition, FIG. 3 shows the correlation between anti-CCP and anti-VCP2 antibodies. 100 RA sera were analyzed with CCP2 test and with VCP2 using the method described in example 2. Results show the significant correlation ($p<0.0001$) between the two populations of antibodies demonstrating that anti-VCP2 antibodies are ACPA and are thus specific for RA and not for other autoimmune diseases.

Example 4

ELISA for the Comparison of Anti-CP of Formula (V) Antibodies and Anti-CP of Formula (VI) Antibodies The ability to recognize specific antibodies in RA patients by MAP of formula (V), in comparison with the MAP of formula (VI) was evaluated by ELISA.

MAP of formula (V) and MAP of formula (VI) were diluted respectively to a concentration of 20 µg/ml and 5 µg/ml in PBS, loaded into the wells of a polystyrene microtitration plate (50 µl/well), and left overnight at +4° C. Upon completion of the coating period, the wells were treated for 1 hour at RT with 3% BSA in PBS. The patients' serum samples (diluted 1:200 in a buffer constituted by 1% BSA, 0.05% Tween X-100 in PBS) were then loaded onto the plate (50 µl/well) and left to incubate for 3 hours at RT. After the incubation period, one washing was performed with 1% PBS Tween X-100 and two washings were performed with PBS (150 µl/well). An anti human-IgG antibody conjugated to the enzyme alkaline phosphatase (50 µl/well), diluted 1:3000 in 1% PBS BSA, 0.05% Tween X-100, was incubated for 3 hours at RT with stirring. Upon completion of the incubation, after three washings as described above, p-nitrophenyl phosphate was added to the wells and the absorbance at a wavelength of 405 nm was determined. The results of the test were expressed as the percentage of positivity, calculated by dividing the absorbance of each serum sample by the absorbance of a positive serum sample the value of which was set arbitrarily at 100.

Serum samples of 100 patients suffering from RA were tested by this method. By considering each result that was greater than the 97.5th percentile of the normal control group to be positive, anti-CP MAP of formula (VI) antibodies were found in 47% of the RA cohort and anti-CP MAP of formula (V) antibodies in 64%. Thus, use of anti-CP MAP of formula (V) antibodies led to a higher sensitivity maintaining the same specificity of 95%.

Example 5

Purification of Anti-CP Antibodies and uses Thereof

Anti-CP antibodies can be purified from serum of RA patients by means of affinity chromatography procedures.

A citrullinated peptide or MAP according to the present invention was conjugated to CNBr-activated sepharose according to standard procedures known by one skilled in the art. Total immunoglobulins from sera containing anti-CP antibodies were precipitated with 50% saturated ammonium sulfate; the precipitates were dissolved in phosphate buffer (pH 7.4) and dialyzed overnight against PBS. Enriched immunoglobulin preparations were applied to the column, and the flowthrough was collected for subsequent analysis. The column was extensively washed with 20 mM $Na_2HPO_4$, 150 mM NaCl (pH 7.2), and the antibodies bound to the column were eluted by 0.1 M glycine buffer (pH 2.8) (0.5 ml/fraction), immediately neutralized with 50 µl Tris 1M (pH 8.0), and dialyzed overnight against PBS. The anti-CP antibody content in the eluates and flowthrough was tested by ELISA.

Such purified antibodies can be used as controls in solid-phase assays using citrullinated antigens.

Figure 4:
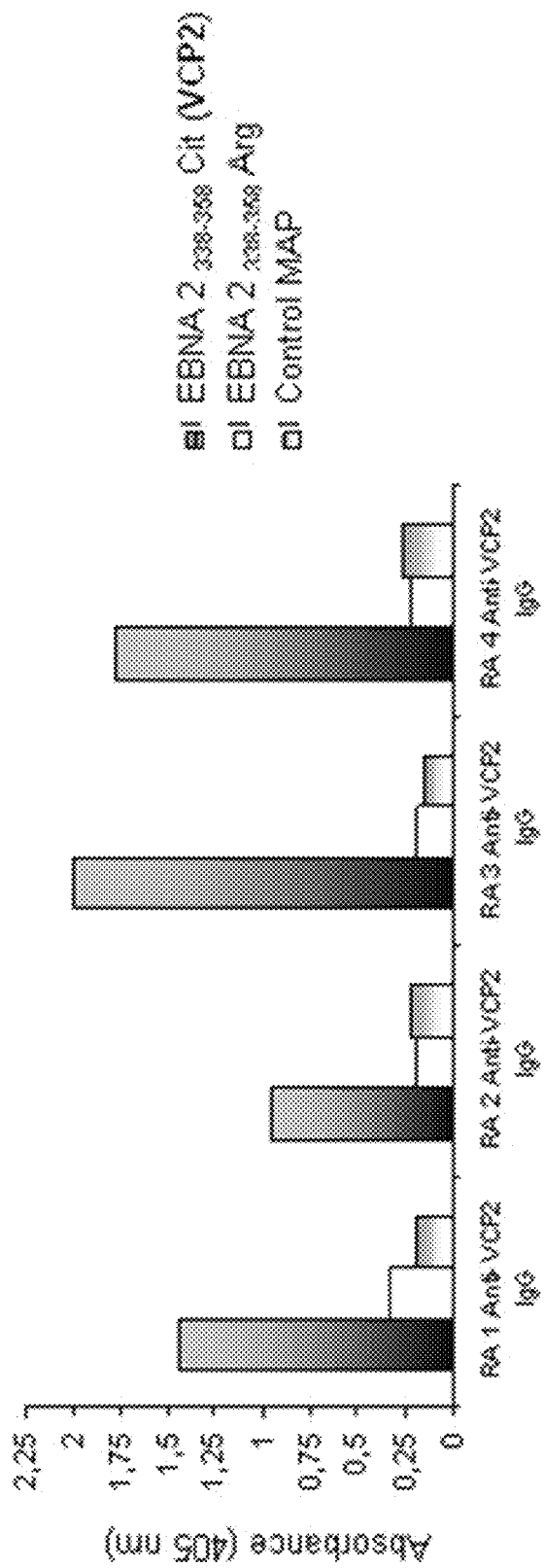
FIG. 4. Isolation of anti-VCP2 antibodies from RA sera was performed according to the method described in example 4. Four preparations of anti-VCP2 antibodies from 4 different RA sera were tested by ELISA onto VCP2, non deiminated EBNA2(338-358) and a control MAP. Anti-VCP2 IgG shows a very high reactivity with VCP2, the citrullinated EBNA2 (338-358) derived MAP, and no binding to arginine containing EBNA2(338-358) and to control MAP.

In addition, four preparations of anti-VCP2 antibodies from 4 different RA sera were tested by ELISA onto VCP2, non deiminated EBNA2(338-358) and a control MAP. Anti-VCP2 IgG shows a very high reactivity with VCP2, the citrullinated EBNA2(338-358) derived MAP, and no binding to arginine containing EBNA2(338-358) and to control MAP (FIG. 4).

Example 6

Role of the Number and Position of Citrullines

The role of the number and of the position of citrullines inside EBNA-2(338-358) sequence in the detection of specific antibodies in RA sera was investigated by means of differently citrullinated peptides (Table 1).

TABLE 1

| Name | Sequence | RA positive sera | NHS positive sera |
| --- | --- | --- | --- |
| EBNA2(338-358) | GQSRGQSRGRGRGRGRGRGKG | 3/24 | 0/23 |
| [Cit³⁴¹]EBNA2(338-358) | GQSCitGQSRGRGRGRGRGRGKG SEQ ID No. 28 | 4/24 | 1/23 |
| [Cit³⁴⁵]EBNA2(338-358) | GQSRGQSCitGRGRGRGRGRGKG SEQ ID No. 4 | 9/24 | 1/23 |
| [Cit³⁴⁷]EBNA2(338-358) | GQSRGQSRGCitGRGRGRGRGKG SEQ ID No. 5 | 6/24 | 1/23 |
| [Cit³⁴⁹]EBNA2(338-358) | GQSRGQSRGRGCitGRGRGRGKG SEQ ID No. 6 | 9/24 | 1/23 |
| [Cit³⁵¹]EBNA2(338-358) | GQSRGQSRGRGRGCitGRGRGKG SEQ ID No. 7 | 6/24 | 1/23 |
| [Cit³⁵³]EBNA2(338-358) | GQSRGQSRGRGRGRGCitGRGKG SEQ ID No. 8 | 6/24 | 0/23 |
| [Cit³⁵⁵]EBNA2(338-358) | GQSRGQSRGRGRGRGRGCitGKG SEQ ID No. 9 | 3/24 | 2/23 |
| [Cit³⁴¹, Cit³⁴⁵]EBNA2(338-358) | GQSCitGQSCitGRGRGRGRGRGKG SEQ ID No. 10 | 12/24 | 0/23 |
| [Cit³⁴⁵, Cit³⁴⁷]EBNA2(338-358) | GQSRGQSCitGCitGRGRGRGRGKG SEQ ID No. 11 | 10/24 | 1/23 |
| [Cit³⁴⁵, Cit³⁴⁹]EBNA2(338-358) | GQSRGQSCitGRGCitGRGRGRGKG SEQ ID No. 12 | 15/24 | 0/23 |
| [Cit³⁴⁵, Cit³⁵¹]EBNA2(338-358) | GQSRGQSCitGRGRGCitGRGRGKG SEQ ID No. 13 | 12/24 | 1/23 |
| [Cit³⁴⁵, Cit³⁵³]EBNA2(338-358) | GQSRGQSCitGRGRGRGCitGRGKG SEQ ID No. 14 | 6/24 | 2/23 |
| [Cit³⁴⁵, Cit³⁵⁵]EBNA2(338-358) | GQSRGQSCitGRGRGRGRGCitGKG SEQ ID No. 15 | 11/24 | 0/23 |
| [Cit³⁴¹, Cit³⁴⁹]EBNA2(338-358) | GQSCitGQSRGRGCitGRGRGRGKG SEQ ID No. 16 | 6/24 | 0/23 |
| [Cit³⁴⁷, Cit³⁴⁹]EBNA2(338-358) | GQSRGQSRGCitGCitGRGRGRGKG SEQ ID No. 17 | 5/24 | 1/23 |
| [Cit³⁴⁹, Cit³⁵¹]EBNA2(338-358) | GQSRGQSRGRGCitGCitGRGRGKG SEQ ID No. 18 | 15/24 | 2/23 |
| [Cit³⁴⁹, Cit³⁵³]EBNA2(338-358) | GQSRGQSRGRGRGCitGCitGRGKG SEQ ID No. 19 | 12/24 | 0/23 |
| [Cit³⁴⁹, Cit³⁵⁵]EBNA2(338-358) | GQSRGQSRGRGRGCitGRGCitGKG SEQ ID No. 20 | 9/24 | 0/23 |
| [Cit³⁴¹, Cit³⁵⁵]EBNA2(338-358) | GQSCitGQSRGRGRGRGRGCitGKG SEQ ID No. 21 | 8/24 | 1/23 |
| [Cit³⁴¹, Cit³⁴⁵, Cit³⁴⁹]EBNA2(338-358) | GQSCitGQSCitGRGCitGRGRGRGKG SEQ ID No. 22 | 12/24 | 1/23 |
| [Cit₃₄₅, Cit³⁴⁷, Cit³⁴⁹]EBNA2(338-358) | GQSRGQSCitGCitGCitGRGRGRGKG SEQ ID No. 23 | 9/24 | 1/23 |
| [Cit³⁴⁵, Cit³⁴⁹, Cit³⁵¹]EBNA2(338-358) | GQSRGQSCitGRGCitGCitGRGRGKG SEQ ID No. 24 | 8/24 | 1/23 |
| [Cit³⁴⁵, Cit³⁴⁹, Cit³⁵³]EBNA2(338-358) | GQSRGQSCitGRGCitGRGCitGRGKG SEQ ID No. 25 | 10/24 | 1/23 |
| [Cit³⁴⁵, Cit³⁴⁹, Cit³⁵⁵]EBNA2(338-358) | GQSRGQSCitGRGCitGRGRGCitGKG SEQ ID No. 26 | 8/24 | 0/23 |

Serum samples of 24 RA patients and 23 normal healthy subjects (NHS) were tested by ELISA using the method described in example 2. By considering each result that was greater than the 97.5th percentile of the normal control group to be positive, it was found that the sensitivity of the test increases according to the number of citrullines and depends on their positions inside the sequence. In details, the not deiminated sequence EBNA-2(338-358) does not recognize IgG antibodies in a relevant number of RA sera (considering the result relevant when the positive RA patient number is higher than 25% of the total RA population). This result is in line with the state of art in the field of RA diagnosis in which it is known that antibodies are directed against citrullinated sequences. The introduction of a single citrulline residue in the EBNA-2(338-358) demonstrates that the positions 345 and 349 are important for recognition since the peptides with either citrullinated position show an increased percentage of positive RA sera. It is believed that these two positions relate to two different antigenic regions.

The introduction of two citrulline residues shows that the peptide [Cit$^{345}$,Cit$^{349}$]EBNA2(338-358) is the most active and selective di-citrullinated peptide. This result confirms that the positions 345 and 349 are important for recognition. It should be noted that the peptide [Cit$^{349}$,Cit$^{351}$] is also very active. However, it is less specific and selective.

Moreover, data obtained for tri-citrullinated EBNA-2(338-358) show that the peptide [Cit$^{341}$,Cit$^{345}$,Cit$^{349}$]EBNA2 (338-358) is the most active peptide in this series. This result further confirms that positions 341, 345 and 349 are important for recognition. It is believed that two epitopes were identified: one in the Gly-Cit repeats and the other in the Gly-Gln-Ser-Cit repeats.

Example 7

Diagnostic Properties of an ELISA Based on the Contemporary use of the MAP of Formula (V) and of the MAP of Formula (VI)

To achieve a highly sensitive immunoassay, an equimolar mixture of MAP of formula (V) and MAP of formula (VI) was allowed to adsorb to 96-wells microtitre plates for 4 h at r.t. The test was then performed as described in example 2.

Using the MAP of formula (V) and the MAP of formula (VI) as coating agents, antibodies can be found in 68% of RA patients. The combined use of citrullinated peptide MAP of formula (V) and citrullinated MAP of formula (VI) improves the diagnostic performances of the single peptide based assays, leading to a RA high sensitive diagnostic assay.

As a matter of facts, in a population of 79 RA patients tested for anti-CCP2, anti-CCP3, and anti-viral citrullinated MAP peptides of formula (V) and (VI), the authors found that 44/79 (56%) are anti-CCP2 positive, 48/79 (61%) are anti-CCP3 positive, 49/79 (62%) react with the peptide of formula (VI) and 41/79 (52%) react with the peptide of formula (V). Noteworthy, 7/79 (9%) anti-CCP2 and anti-CCP3 negative sera are positive to the peptide of formula (VI); 2/79 (3%) anti-CCP2 and anti-CCP3 negative sera are positive to peptide of formula (V); 1/79 (1%) anti-CCP2 and anti-CCP3 negative serum is positive to both peptides of formula (V) and formula (VI). Thus, formula (V) and (VI) allow to detect antibodies in a subgroup of anti-CCP negative RA patients (FIG. 1).

Comparing the results obtained with MAP of formula (V) and MAP of formula (VI), it was found that most of RA sera contain antibodies reacting with both MAP. Nonetheless, 15% of RA sera contain antibodies reacting with either one of the two deiminated MAP of formula (V) and (VI), thus suggesting that the two antibody populations are overlapped but different.

T-Cell Response

The inventors have also found that the citrullinated peptides of the invention are capable of specifically recognizing not only anti-CP antibodies as described above, but also T cells specific to citrullinated peptides. T cells specific to citrullinated peptides are characteristic of some autoimmune diseases in which there is a cell-mediated immune response to citrullinated antigens. For example, in multiple sclerosis (MS), the existence of T cells specific to the basic protein of deiminated myelin (MBP) has been demonstrated [L. R. Tranquill et al., Mult. Scler. 2000, 6, 220].

The citrullinated synthetic peptides of the invention, both in linear form and in MAP form, can therefore be used as antigens for the detection of T cells specific to citrullinated antigens.

The type of assay commonly used to detect antigen-specific T cells is the proliferation test in which peripheral blood leukocytes of a patient to be examined are grown together with graduated doses of the antigen, in this case a citrullinated synthetic peptide as described above. If the patient has previously encountered citrullinated peptides and has a sufficient number of T cells specific thereto, proliferation will be achieved in the presence of this antigen.

As expected, in the test, it is necessary to introduce a substance capable of inducing proliferation of all of the T cells (a mitogen) as a positive control, as well as some antigens against which the patient is assumed not to have been immunized, as a negative control.

The citrullinated peptides of the invention, particularly in MAP form, are optimal antigens for this type of assay. It is in fact known that the polymeric structure of MAPs facilitates their processing and presentation to T cells.

The antigen-specific T cells can then be morphologically and functionally characterized e.g. they can be analyzed by cytofluorometry for the expression of surface molecules and the production of cytokines.

Therapeutic Use

Finally, the citrullinated peptides of the invention, both in linear form and in MAP form, can also be used as modulators of the immune response in autoimmune diseases, for example RA. The citrullinated synthetic peptides of the invention can be used for the treatment of patients affected by RA, MS, or other autoimmune diseases in which the existence of a cell-mediated immune response to deiminated antigens has been demonstrated.

The invention claimed is:

1. An antigenically effective peptide comprising, from the amino to the carboxylic terminal, the amino acid sequence:

G Q S $X_1$ G Q S $X_2$ G $X_3$ G $X_4$ G $X_5$ G $X_6$ G $X_7$ G K G (residues 19 to 39 of SEQ ID No. 1)

wherein the amino acids $X_1$-$X_7$ are selected independently from the group consisting of an arginine residue and a citrulline residue, and at least one of $X_1$-$X_7$ is a citrulline residue, wherein said peptide is in linear form or in a form of a multimeric branched peptide.

2. The peptide of claim 1, comprising the amino acid sequence G Q S Cit G Q S Cit G $X_3$ G Cit G $X_5$ G $X_6$ G $X_7$ G K G (SEQ ID No. 27)

wherein the amino acids $X_3$, $X_5$, $X_6$ and $X_7$ are selected independently from an arginine residue or a citrulline residue.

3. The peptide of claim 1, comprising the sequence selected from the group consisting of:

```
                                        (SEQ ID No. 4)
GQSRGQSCitGRGRGRGRGRGKG, (SEQ ID No. 6)
GQSRGQSRGRGCitGRGRGRGKG, (SEQ ID No. 12)
GQSRGQSCitGRGCitGRGRGRGKG, (SEQ ID No. 22)
GQSCitGQSCitGRGCitGRGRGRGKG
and (SEQ ID No. 2)
G Q S Cit G Q S Cit G Cit G Cit G Cit G Cit G Cit G K G
``` wherein
Cit is a citrulline residue.

4. The multimeric branched peptide of claim 1, comprising four identical copies of the peptide.

5. The multimeric branched peptide of claim 4 being (G Q S Cit G Q S Cit G Cit G Cit G Cit G Cit G Cit G K G)$_4$ K$_2$ K beta-Alanine:

wherein
Cit is a citrulline residue.

6. A method of diagnosing an autoimmune disease in a subject comprising detecting antibodies specific for the autoimmune disease in a biological sample obtained from the subject by
(a) reacting the biological sample under conditions suitable for the formation of immune complexes with the peptide of claim 1, to produce a complex,
(b) reacting the complex formed in (a) with a labeled antibody specific for human immunoglobulins and
(c) detecting the labeled complex of (b) to determine the presence of an autoimmune disease.

7. The method of claim 6, step (a), further comprising reacting the biological sample with a peptide consisting of the sequence (G G D N H G Cit G Cit G Cit G Cit G Cit G G G Cit P GAP G)$_4$ K$_2$ K beta-Alanine:

wherein Cit is citrulline,
to produce a complex.

8. The method of claim 6 comprising
(a) reacting the biological sample under conditions suitable for the formation of an immune complex with a peptide consisting of (G Q S Cit G Q S Cit G Cit G Cit G Cit G Cit G Cit G K G)$_4$ K$_2$ K beta-Alanine:

wherein Cit is citrulline, and also reacting the biological sample with a peptide consisting of (G G D N H G Cit G Cit G Cit G Cit G Cit G G G Cit P G A P G)$_4$ K$_2$ K betaAlanine:

wherein Cit is citrulline,
to produce a complex,
(b) reacting the complex formed in (a) with a labeled antibody specific for human immunoglobulins and
(c) detecting the labeled complex of (b) to determine the presence of an autoimmune disease.

9. The method of claim 6 being an immunological assay.

10. A kit for diagnosing an autoimmune disease comprising at least one antigenically effective peptide of claim 1, and at least one further reagent.

11. The kit of claim 10 further comprising a peptide consisting of the sequence (G G D N H G Cit G Cit G Cit G Cit G Cit G G G Cit P GAP G)$_4$ K$_2$ K beta-Alanine:

G G D N H G Cit G Cit G Cit G Cit G Cit G G G Cit P G A P G\
                                                                     K\
G G D N H G Cit G Cit G Cit G Cit G Cit G G G Cit P G A P G\
                                                                     K-betaA\
G G D N H G Cit G Cit G Cit G Cit G Cit G G G Cit P G A P G\
                                                                     K\
G G D N H G Cit G Cit G Cit G Cit G Cit G G G Cit P G A P G wherein Cit is citrulline.

12. The method of claim 6 wherein the autoimmune disease is rheumatoid arthritis.

\* \* \* \* \*

SEQUENCE LISTING

```
<160> NUMBER OF SEQ ID NOS: 28

<210> SEQ ID NO 1
<211> LENGTH: 56
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MISC_FEATURE
<222> LOCATION: (22)..(22)
<223> OTHER INFORMATION: arginine or citrulline residue
<220> FEATURE:
<221> NAME/KEY: MISC_FEATURE
<222> LOCATION: (26)..(26)
<223> OTHER INFORMATION: arginine or citrulline residue
<220> FEATURE:
<221> NAME/KEY: MISC_FEATURE
<222> LOCATION: (28)..(28)
<223> OTHER INFORMATION: arginine or citrulline residue
<220> FEATURE:
<221> NAME/KEY: MISC_FEATURE
<222> LOCATION: (30)..(30)
<223> OTHER INFORMATION: arginine or citrulline residue
<220> FEATURE:
<221> NAME/KEY: MISC_FEATURE
<222> LOCATION: (32)..(32)
<223> OTHER INFORMATION: arginine or citrulline residue
<220> FEATURE:
<221> NAME/KEY: MISC_FEATURE
<222> LOCATION: (34)..(34)
<223> OTHER INFORMATION: arginine or citrulline residue
<220> FEATURE:
<221> NAME/KEY: MISC_FEATURE
<222> LOCATION: (36)..(36)
<223> OTHER INFORMATION: arginine or citrulline residue
<220> FEATURE:
<221> NAME/KEY: MISC_FEATURE
<222> LOCATION: (42)..(42)
<223> OTHER INFORMATION: arginine or citrulline residue
<220> FEATURE:
<221> NAME/KEY: MISC_FEATURE
<222> LOCATION: (46)..(46)
<223> OTHER INFORMATION: arginine or citrulline residue
<220> FEATURE:
<221> NAME/KEY: MISC_FEATURE
<222> LOCATION: (53)..(53)
<223> OTHER INFORMATION: arginine or citrulline residue

<400> SEQUENCE: 1

Gly Pro Pro Trp Trp Pro Pro Ile Cys Asp Pro Pro Gln Pro Ser Lys
1               5                   10                  15

Thr Gln Gly Gln Ser Xaa Gly Gln Ser Xaa Gly Xaa Gly Xaa Gly Xaa
            20                  25                  30

Gly Xaa Gly Xaa Gly Lys Gly Lys Ser Xaa Asp Lys Gln Xaa Lys Pro
        35                  40                  45

Gly Gly Pro Trp Xaa Pro Glu Pro
    50                  55

<210> SEQ ID NO 2
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: citrulline residue
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (10)..(10)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue
```

```
<220> FEATURE:
<221> NAME/KEY: MISC_FEATURE
<222> LOCATION: (14)..(14)
<223> OTHER INFORMATION: citrulline residue
<220> FEATURE:
<221> NAME/KEY: MISC_FEATURE
<222> LOCATION: (16)..(16)
<223> OTHER INFORMATION: citrulline residue
<220> FEATURE:
<221> NAME/KEY: MISC_FEATURE
<222> LOCATION: (18)..(18)
<223> OTHER INFORMATION: citrulline residue

<400> SEQUENCE: 2

Gly Gln Ser Xaa Gly Gln Ser Xaa Gly Xaa Gly Xaa Gly Xaa Gly Xaa
1               5                   10                  15

Gly Xaa Gly Lys Gly
            20

<210> SEQ ID NO 3
<211> LENGTH: 24
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: citrulline residue
<220> FEATURE:
<221> NAME/KEY: MISC_FEATURE
<222> LOCATION: (9)..(9)
<223> OTHER INFORMATION: citrulline residue
<220> FEATURE:
<221> NAME/KEY: MISC_FEATURE
<222> LOCATION: (11)..(11)
<223> OTHER INFORMATION: citrulline residue
<220> FEATURE:
<221> NAME/KEY: MISC_FEATURE
<222> LOCATION: (13)..(13)
<223> OTHER INFORMATION: citrulline residue
<220> FEATURE:
<221> NAME/KEY: MISC_FEATURE
<222> LOCATION: (15)..(15)
<223> OTHER INFORMATION: citrulline residue
<220> FEATURE:
<221> NAME/KEY: MISC_FEATURE
<222> LOCATION: (19)..(19)
<223> OTHER INFORMATION: citrulline residue

<400> SEQUENCE: 3

Gly Gly Asp Asn His Gly Xaa Gly Xaa Gly Xaa Gly Xaa Gly Xaa Gly
1               5                   10                  15

Gly Gly Xaa Pro Gly Ala Pro Gly
            20

<210> SEQ ID NO 4
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<223> OTHER INFORMATION: arginine or citrulline residue
<220> FEATURE:
<221> NAME/KEY: MISC_FEATURE
<222> LOCATION: (8)..(8)
<223> OTHER INFORMATION: citrulline residue
```

-continued

<400> SEQUENCE: 4

Gly Gln Ser Arg Gly Gln Ser Xaa Gly Arg Gly Arg Gly Arg
1               5                   10                  15

Gly Arg Gly Lys Gly
            20

<210> SEQ ID NO 5
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: citrulline residue

<400> SEQUENCE: 5

Gly Gln Ser Arg Gly Gln Ser Arg Gly Xaa Gly Arg Gly Arg
1               5                   10                  15

Gly Arg Gly Lys Gly
            20

<210> SEQ ID NO 6
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: citrulline residue

<400> SEQUENCE: 6

Gly Gln Ser Arg Gly Gln Ser Arg Gly Arg Gly Xaa Gly Arg
1               5                   10                  15

Gly Arg Gly Lys Gly
            20

<210> SEQ ID NO 7
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: citrulline residue

<400> SEQUENCE: 7

Gly Gln Ser Arg Gly Gln Ser Arg Gly Arg Gly Arg Gly Xaa Gly Arg
1               5                   10                  15

Gly Arg Gly Lys Gly
            20

<210> SEQ ID NO 8
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: citrulline residue

```
<400> SEQUENCE: 8

Gly Gln Ser Arg Gly Gln Ser Arg Gly Arg Gly Arg Gly Arg Gly Xaa
1               5                   10                  15

Gly Arg Gly Lys Gly
            20

<210> SEQ ID NO 9
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (18)..(18)
<223> OTHER INFORMATION: citrulline residue

<400> SEQUENCE: 9

Gly Gln Ser Arg Gly Gln Ser Arg Gly Arg Gly Arg Gly Arg Gly Arg
1               5                   10                  15

Gly Xaa Gly Lys Gly
            20

<210> SEQ ID NO 10
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: citrulline residue
<220> FEATURE:
<221> NAME/KEY: MISC_FEATURE
<222> LOCATION: (8)..(8)
<223> OTHER INFORMATION: citrulline residue

<400> SEQUENCE: 10

Gly Gln Ser Xaa Gly Gln Ser Xaa Gly Arg Gly Arg Gly Arg Gly Arg
1               5                   10                  15

Gly Arg Gly Lys Gly
            20

<210> SEQ ID NO 11
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (10)..(10)
<223> OTHER INFORMATION: citrulline residue

<400> SEQUENCE: 11

Gly Gln Ser Arg Gly Gln Ser Xaa Gly Xaa Gly Arg Gly Arg Gly Arg
1               5                   10                  15

Gly Arg Gly Lys Gly
            20
```

```
<210> SEQ ID NO 12
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue

<400> SEQUENCE: 12

Gly Gln Ser Arg Gly Gln Ser Xaa Gly Arg Gly Xaa Gly Arg Gly Arg
1               5                   10                  15

Gly Arg Gly Lys Gly
            20

<210> SEQ ID NO 13
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (14)..(14)
<223> OTHER INFORMATION: citrulline residue

<400> SEQUENCE: 13

Gly Gln Ser Arg Gly Gln Ser Xaa Gly Arg Gly Arg Gly Xaa Gly Arg
1               5                   10                  15

Gly Arg Gly Lys Gly
            20

<210> SEQ ID NO 14
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (16)..(16)
<223> OTHER INFORMATION: citrulline residue

<400> SEQUENCE: 14

Gly Gln Ser Arg Gly Gln Ser Xaa Gly Arg Gly Arg Gly Arg Gly Xaa
1               5                   10                  15

Gly Arg Gly Lys Gly
            20

<210> SEQ ID NO 15
<211> LENGTH: 21
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (18)..(18)
<223> OTHER INFORMATION: citrulline residue

<400> SEQUENCE: 15

Gly Gln Ser Arg Gly Gln Ser Xaa Gly Arg Gly Arg Gly Arg Gly Arg
1               5                   10                  15

Gly Xaa Gly Lys Gly
            20

<210> SEQ ID NO 16
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: citrulline residue
<220> FEATURE:
<221> NAME/KEY: MISC_FEATURE
<222> LOCATION: (14)..(14)
<223> OTHER INFORMATION: citrulline residue

<400> SEQUENCE: 16

Gly Gln Ser Xaa Gly Gln Ser Arg Gly Arg Gly Arg Gly Xaa Gly Arg
1               5                   10                  15

Gly Arg Gly Lys Gly
            20

<210> SEQ ID NO 17
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: citrulline residue
<220> FEATURE:
<221> NAME/KEY: MISC_FEATURE
<222> LOCATION: (14)..(14)
<223> OTHER INFORMATION: citrulline residue

<400> SEQUENCE: 17

Gly Gln Ser Arg Gly Gln Ser Arg Gly Xaa Gly Arg Gly Xaa Gly Arg
1               5                   10                  15

Gly Arg Gly Lys Gly
            20

<210> SEQ ID NO 18
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: citrulline residue
```

```
<220> FEATURE:
<221> NAME/KEY: MISC_FEATURE
<222> LOCATION: (14)..(14)
<223> OTHER INFORMATION: citrulline residue

<400> SEQUENCE: 18

Gly Gln Ser Arg Gly Gln Ser Arg Gly Arg Gly Xaa Gly Xaa Gly Arg
1               5                   10                  15

Gly Arg Gly Lys Gly
            20

<210> SEQ ID NO 19
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: citrulline residue
<220> FEATURE:
<221> NAME/KEY: MISC_FEATURE
<222> LOCATION: (16)..(16)
<223> OTHER INFORMATION: citrulline residue

<400> SEQUENCE: 19

Gly Gln Ser Arg Gly Gln Ser Arg Gly Arg Gly Arg Gly Xaa Gly Xaa
1               5                   10                  15

Gly Arg Gly Lys Gly
            20

<210> SEQ ID NO 20
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: citrulline residue
<220> FEATURE:
<221> NAME/KEY: MISC_FEATURE
<222> LOCATION: (18)..(18)
<223> OTHER INFORMATION: citrulline residue

<400> SEQUENCE: 20

Gly Gln Ser Arg Gly Gln Ser Arg Gly Arg Gly Arg Gly Xaa Gly Arg
1               5                   10                  15

Gly Xaa Gly Lys Gly
            20

<210> SEQ ID NO 21
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: citrulline residue
<220> FEATURE:
<221> NAME/KEY: MISC_FEATURE
<222> LOCATION: (18)..(18)
<223> OTHER INFORMATION: citrulline residue
```

<400> SEQUENCE: 21

Gly Gln Ser Xaa Gly Gln Ser Arg Gly Arg Gly Arg Gly Arg
1               5                   10                  15

Gly Xaa Gly Lys Gly
            20

<210> SEQ ID NO 22
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: citrulline residue
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue

<400> SEQUENCE: 22

Gly Gln Ser Xaa Gly Gln Ser Xaa Gly Arg Gly Xaa Gly Arg Gly Arg
1               5                   10                  15

Gly Arg Gly Lys Gly
            20

<210> SEQ ID NO 23
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (10)..(10)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue

<400> SEQUENCE: 23

Gly Gln Ser Arg Gly Gln Ser Xaa Gly Xaa Gly Xaa Gly Arg Gly Arg
1               5                   10                  15

Gly Arg Gly Lys Gly
            20

<210> SEQ ID NO 24
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue

```
<220> FEATURE:
<221> NAME/KEY: MISC_FEATURE
<222> LOCATION: (14)..(14)
<223> OTHER INFORMATION: citrulline residue

<400> SEQUENCE: 24

Gly Gln Ser Arg Gly Gln Ser Xaa Gly Arg Gly Xaa Gly Xaa Gly Arg
1               5                   10                  15

Gly Arg Gly Lys Gly
            20

<210> SEQ ID NO 25
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue
<220> FEATURE:
<221> NAME/KEY: MISC_FEATURE
<222> LOCATION: (16)..(16)
<223> OTHER INFORMATION: citrulline residue

<400> SEQUENCE: 25

Gly Gln Ser Arg Gly Gln Ser Xaa Gly Arg Gly Xaa Gly Arg Gly Xaa
1               5                   10                  15

Gly Arg Gly Lys Gly
            20

<210> SEQ ID NO 26
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (12)..(12)
<223> OTHER INFORMATION: citrulline residue
<220> FEATURE:
<221> NAME/KEY: MISC_FEATURE
<222> LOCATION: (18)..(18)
<223> OTHER INFORMATION: citrulline residue

<400> SEQUENCE: 26

Gly Gln Ser Arg Gly Gln Ser Xaa Gly Arg Gly Xaa Gly Arg Gly Arg
1               5                   10                  15

Gly Xaa Gly Lys Gly
            20

<210> SEQ ID NO 27
<211> LENGTH: 21
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MISC_FEATURE
<222> LOCATION: (4)..(4)
<223> OTHER INFORMATION: citrulline residue
<220> FEATURE:
<221> NAME/KEY: MISC_FEATURE
<222> LOCATION: (8)..(8)
<223> OTHER INFORMATION: citrulline residue
<220> FEATURE:
<221> NAME/KEY: MISC_FEATURE
<222> LOCATION: (10)..(10)
<223> OTHER INFORMATION: arginine or citrulline residue
<220> FEATURE:
<221> NAME/KEY: MISC_FEATURE
<222> LOCATION: (12)..(12)
<223> OTHER INFORMATION: citrulline residue
<220> FEATURE:
<221> NAME/KEY: MISC_FEATURE
<222> LOCATION: (14)..(14)
<223> OTHER INFORMATION: arginine or citrulline residue
<220> FEATURE:
<221> NAME/KEY: MISC_FEATURE
<222> LOCATION: (16)..(16)
<223> OTHER INFORMATION: arginine or citrulline residue
<220> FEATURE:
<221> NAME/KEY: MISC_FEATURE
<222> LOCATION: (18)..(18)
<223> OTHER INFORMATION: arginine or citrulline residue

<400> SEQUENCE: 27

Gly Gln Ser Xaa Gly Gln Ser Xaa Gly Xaa Gly Xaa Gly Xaa Gly Xaa
1               5                   10                  15

Gly Xaa Gly Lys Gly
            20

<210> SEQ ID NO 28
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: citrulline residue

<400> SEQUENCE: 28

Gly Gln Ser Xaa Gly Gln Ser Arg Gly Arg Gly Arg Gly Arg Gly Arg
1               5                   10                  15

Gly Arg Gly Lys Gly
            20
```